US009700506B2

(12) United States Patent
Kim et al.

(10) Patent No.: US 9,700,506 B2
(45) Date of Patent: Jul. 11, 2017

(54) **ANTIOXIDANT COMPOSITION CONTAINING EXTRACT OF PROCESSED *CHRYSANTHEMUM INDICUM* OR *CITRUS UNSHIU* PEEL**

(75) Inventors: Dong Hyun Kim, Suwon-si (KR); Jun Seong Park, Suwon-si (KR); Jae Kyoung Lee, Seoul (KR); Hye Yoon Park, Anyang-si (KR); Soo Mi Ahn, Suwon-si (KR); Duck Hee Kim, Seoul (KR); Han Kon Kim, Suwon-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 1339 days.

(21) Appl. No.: 13/128,700

(22) PCT Filed: Nov. 19, 2009

(86) PCT No.: PCT/KR2009/006837
§ 371 (c)(1),
(2), (4) Date: May 11, 2011

(87) PCT Pub. No.: WO2010/058984
PCT Pub. Date: May 27, 2010

(65) Prior Publication Data
US 2011/0223265 A1 Sep. 15, 2011

(30) Foreign Application Priority Data

Nov. 19, 2008 (KR) .......................... 10-2008-0115369

(51) Int. Cl.
*A61K 36/752* (2006.01)
*A61K 36/287* (2006.01)
*A61K 8/97* (2017.01)
*A61K 8/02* (2006.01)
*A61Q 19/00* (2006.01)

(52) U.S. Cl.
CPC .............. *A61K 8/97* (2013.01); *A61K 8/0212* (2013.01); *A61Q 19/00* (2013.01); *A61K 2800/522* (2013.01)

(58) Field of Classification Search
None
See application file for complete search history.

(56) References Cited

U.S. PATENT DOCUMENTS

| 6,726,940 B2 * | 4/2004 | Martin et al. ................. 424/764 |
| 2003/0138511 A1 * | 7/2003 | Yamamoto ............... A23G 3/36 |
| | | 424/777 |
| 2004/0223942 A1 * | 11/2004 | Fujimura ........................ 424/74 |

FOREIGN PATENT DOCUMENTS

| JP | 63170323 A | * | 7/1988 |
| JP | 09023850 A | * | 1/1997 |

OTHER PUBLICATIONS

International Search Report for PCT/KR2009/006837, dated Aug. 9, 2010.
Written Opinion for PCT/KR2009/006837, dated Aug. 9, 2010.
Jung Sik You et al., "Quality characteristics of *Chrysathemum indicum* L. Flower Tea in relation to the number of pan-firing", *J. Korean Soc. Food. Sci. Nutr.*, May 31, 2008, 37(5), pp. 647-652 (Abstract).
Kyung Mi Yoo et al., "Antioxidant activity and physiochemical Characteristics of Tangerine peel tea prepared with Citrus unshiu cultivated in Cheju", *Korean J. Food Cookery Sci.*, Jun. 2005, 21(3), pp. 354-359 (Abstract).
Bae Cheon Cha et al., "Antioxidative effect of domestic plants", *Kor. J. Pharmacogn.*, 1997, 28(1), pp. 15-20 (Abstract).
Sung Je Jung et al., "Screening for antioxidant activity of plant medicinal extracts", *J. Korean Soc. Appl. Biol. Chem.*, 2004, 47(1), pp. 135-140 (Abstract).
English translation of CN Office Action and CN Office Action dated Jul. 4, 2012.
Zheng et al, Research on Pericarpium Citri Reticulatae, Modern Chinese Medicine, vol. 9, No. 10, Oct. 31, 2007.
Hu Xilan et al, Antioxidant Activity Detection of 17 Plant Samples by Using DPPH Method, Food Science and Technology, No. 10, Dec. 31, 2006.

* cited by examiner

*Primary Examiner* — Terry A McKelvey
*Assistant Examiner* — Catheryne Chen
(74) *Attorney, Agent, or Firm* — Nixon & Vanderhye P.C.

(57) ABSTRACT

The present invention relates to an antioxidant cosmetic composition, and more particularly to an antioxidant cosmetic composition containing, as an active ingredient, either an extract of at least one of *Chrysanthemum indicum* and *Citrus unshiu* peel, processed using a medicinal herb processing technique, or a mixture of said extract and an extract of at least one of unprocessed *Chrysanthemum indicum* and *Citrus unshiu* peel.

10 Claims, No Drawings

\# ANTIOXIDANT COMPOSITION CONTAINING EXTRACT OF PROCESSED *CHRYSANTHEMUM INDICUM* OR *CITRUS UNSHIU* PEEL

This application is the U.S. national phase of International Application No. PCT/KR2009/006837 filed 19 Nov. 2009 which designated the U.S. and claims priority to KR 10-2008-0115369 filed 19 Nov. 2008, the entire contents of each of which are hereby incorporated by reference.

TECHNICAL FIELD

The present invention relates to an antioxidant cosmetic composition, and more particularly to an antioxidant cosmetic composition containing, as an active ingredient, either an extract of at least one of *Chrysanthemum indicum* and *Citrus unshiu* peel, processed using a medicinal herb processing technique, or a mixture of said extract and an extract of at least one of unprocessed *Chrysanthemum indicum* and *Citrus unshiu* peel.

BACKGROUND ART

A medicinal herb processing technique that is a traditional Chinese medicine manufacturing technique is called "Po-je", "Hap-hwa", "Hap-yak", "Su-chi", "Po-ja", "Bub-je" and "Su-sa" in Korean. This technique can be defined as a medicine manufacturing technique of changing the inherent properties of medicinal herbs by processing the medicinal herbs on the basis of the Chinese medicine theory.

The objects of processing medicinal herbs are to clarify medicines, facilitate the storage of medicines, reduce or remove the toxicity or side effects of medicines, change the properties of medicines to make the medicines more effective, enhance the therapeutic effects of medicines, and the offensive odor and taste of medicines to facilitate the intake of the medicines.

Meanwhile, in the manufacture of cosmetic products, raw materials having various effects, including skin whitening, wrinkle reduction and skin protection, are screened and added. Among these effects, the antioxidant effect removes reactive oxygen species, which are the cause of skin aging, to retard or prevent skin aging, changes a dull and inelastic skin to a fresh and clear skin, and makes the skin to look healthy in appearance. However, only a limited number of materials are known to have the antioxidant effect, and a small number of materials which are currently being used are chemically synthesized.

Recently, various cosmetic products which employ natural materials in order to reduce skin irritation caused by various chemical substances have been developed. In addition, natural materials have reduced side effects on the skin and receive a great deal of attention from consumers. Thus, many efforts to develop natural materials useful as cosmetic raw materials are being made.

DISCLOSURE OF INVENTION

Technical Problem

Accordingly, the present inventors have conducted studies on natural materials having excellent antioxidant effects and, as a result, have found that, when a cosmetic composition is prepared using an extract of processed *Chrysanthemum indicum* or *Citrus unshiu* peel alone or in a mixture with an extract of unprocessed *Chrysanthemum indicum* or *Citrus unshiu* peel, the prepared composition shows a very excellent antioxidant effect, thereby completing the present invention.

It is therefore an object of the present invention to provide a cosmetic composition having an excellent antioxidant effect.

Solution to Problem

To achieve the above object, the present invention provides an antioxidant cosmetic composition containing, as an active ingredient, an extract of at least one of processed *Chrysanthemum indicum* and *Citrus unshiu* peel.

The present invention provides an antioxidant cosmetic composition containing a mixture of an extract of at least one of processed *Chrysanthemum indicum* and *Citrus unshiu* peel and an extract of at least one of unprocessed *Chrysanthemum indicum* and *Citrus unshiu* peel.

Advantageous Effects of Invention

The cosmetic composition according to the present invention contains an extract of at least one of processed *Chrysanthemum indicum* and *Citrus unshiu* peel alone or in a mixture with an extract of at least one of unprocessed *Chrysanthemum indicum* and *Citrus unshiu* peel, and thus has an excellent antioxidant effect of inhibiting DPPH oxidation.

Best Mode for Carrying out the Invention

The present invention relates to an antioxidant cosmetic composition containing, as an active ingredient, an extract of at least one of processed *Chrysanthemum indicum* and *Citrus unshiu* peel.

The present invention also relates to an antioxidant cosmetic composition containing a mixture of an extract of at least one of processed *Chrysanthemum indicum* and *Citrus unshiu* peel and an extract of at least one of unprocessed *Chrysanthemum indicum* and *Citrus unshiu* peel. Herein, the extract of the unprocessed plant, which is mixed with the extract of the processed plant, is prepared from a plant different from a plant used to prepare the extract of the processed plant. For example, a cosmetic composition according to a preferred embodiment of the present invention may contain, as active ingredients, an extract of unprocessed *Chrysanthemum indicum* and an extract of processed *Citrus unshiu* peel.

As used herein, the term "extract of the unprocessed plant" refers to an extract obtained by extracting *Chrysanthemum indicum* or *Citrus unshiu* peel with water or an organic solvent, which are conventionally used, without processing the plant.

Hereinafter, the present invention will be described in detail.

*Chrysanthemum indicum* which is used in the present invention is called "Hwang-kook" or "Gam-kook" in Korean. This plant grows mainly in the mountains and has short hairs throughout thereof. The stem reaches a height of 60-90 cm and is black, slender and long. Umbel flower heads open on the upper portion of the stem in September to October. In Chinese medicine, the plant is used to treat a fever, pneumonia, bronchitis, headache, gastritis, enteritis, a swell and the like. In folk remedies, the plant is attached to the affected area of the body in a pulverized state, or the affected area is washed with a liquid obtained by boiling the plant in water. In the present invention, in consideration of problems such as difficulty in storage (decomposition) or the quantitative decrease of effective extracts, the flower of *Chrysanthemum indicum* is used in a dried form, but the scope of the present invention is not limited thereto.

*Citrus unshiu* peel which is used in the present invention refers to the peel of *Citrus unshiu* Markovich and is generally obtained by harvesting and drying *Citrus unshiu* Markovich in October to November. It contains volatile essential oil, hesperidin (flavone glycoside), citric acid, vitamin $B_1$ and the like. *Citrus unshiu* peel is described in the literature as follows. *Citrus unshiu* peel is warm in nature, nontoxic, and hot and bitter in taste. It acts mainly in the spleen meridian and also acts in the lung meridian and the stomach meridian. It is used for abdominal bloating and discomfort, caused by indigestion, and the stagnation of qi in the spleen and stomach, which leads to anorexia, nausea, vomiting and the like. It is also used for a cough with much phlegm and is effective in alleviating damp phlegm conditions, which produce much thick white phlegm and cause discomfort in the chest and abdomen.

The cosmetic composition according to the present invention is characterized in that it contains extracts prepared by processing each of *Chrysanthemum indicum* and *Citrus unshiu* peel and extracting each of the processed plants with an organic solvent.

Extracts of *Chrysanthemum indicum* and *Citrus unshiu* peel can be prepared through a method comprising the steps of:

a) adding honey to *Chrysanthemum indicum* or *Citrus unshiu* peel and allowing the added honey to be absorbed into the plant for 30 minutes to 1 hour;

b) roasting the plant of step a) at 100-180° C. for 10 minutes to 1 hour; and c) extracting the roasted *Chrysanthemum indicum* or *Citrus unshiu* peel of step b) with an organic solvent.

The honey in step a) is added in an amount of 20-30 wt % based on the weight of *Chrysanthemum indicum* or *Citrus unshiu* peel used.

The extraction in step c) can be carried out according to any conventional method known in the art. For example, an extract of each of the *Chrysanthemum indicum* and *Citrus unshiu* peel can be obtained by adding water or an organic solvent to each of *Chrysanthemum indicum* and *Citrus unshiu* peel, extracting the plant under reflux in the solvent, dipping the extract in the solvent, filtering the extract through filter cloth, centrifuging the filtered extract to separate it into the residue and the filtrate, and concentrating the separated filtrate under reduced pressure. The organic solvent which is used in the present invention can be selected from the group consisting of ethanol, methanol, butanol, ether, ethyl acetate, chloroform, and mixtures of these solvents with water. Preferably, 80% ethanol is used. Herein, the extraction temperature is preferably 10-80° C., and the extraction time is preferably 6-24 hours. If the extraction temperature and time are out of the above-specified ranges, the extraction efficiency can be reduced or the changes in the components of the extract can occur.

After the extract has been obtained using the solvent as described above, the extract may be macerated at room temperature according to a conventional method known in the art, and the macerated extract may be heated and filtered, thus obtaining a liquid-phase material. Alternatively, the extract may additionally be evaporated to remove the solvent or be spray-dried or freeze-dried.

The cosmetic composition according to the present invention contains one or a mixture of the extracts of processed *Chrysanthemum indicum* and *Citrus unshiu* peel in an amount of 0.0001-30 wt % based on the total weight of the composition. If the content of the extract in the cosmetic composition is less than 0.0001 wt %, the antioxidant effect of the extract cannot be obtained, and if the content exceeds 30 wt %, the increase in the content will not lead to a significant increase in the effect of the extract and it will be difficult to maintain stability or prepare a formulation.

When the mixture of the extracts of processed *Chrysanthemum indicum* and *Citrus unshiu* peel is used, the mixture is preferably contained in an amount of 0.0001-30 wt % based on the total weight of the composition, and each of the components of the mixture may be used in an amount suitably selected from the range of 0.0001 to 30 wt % based on total weight of the composition. Preferably, the extracts of processed *Chrysanthemum indicum* and *Citrus unshiu* peel are used at a weight ratio of 1:1.

Also, the cosmetic composition according to the present invention may contain, in addition to the extract of at least one of processed *Chrysanthemum indicum* and *Citrus unshiu* peel, an extract of at least one of unprocessed *Chrysanthemum indicum* and *Citrus unshiu* peel.

The extract of unprocessed *Chrysanthemum indicum* or *Citrus unshiu* peel is prepared by extracting *Chrysanthemum indicum* or *Citrus unshiu* peel with water or an organic solvent without processing the plant, and the preparation process thereof is the same as the above-described extraction process of step c). Herein, the extract of the unprocessed plant, which is mixed with the extract of the processed plant, is prepared from a plant different from a plant used to prepare the extract of the processed plant.

Furthermore, the cosmetic composition according to the present invention contains an extract of at least one of processed *Chrysanthemum indicum* and *Citrus unshiu* peel and an extract of unprocessed *Chrysanthemum indicum* and *Citrus unshiu* peel in an amount of 0.0001-30 wt % based on the total weight of the composition. If the content of the extracts in the composition is less than 0.0001 wt %, the antioxidant effect of the extract cannot be obtained, and if the content exceeds 30 wt %, the increase in the content will not lead to a significant increase in the effects of the extracts and it will be difficult to maintain stability or prepare a formulation.

When the mixture of the extract of processed *Chrysanthemum indicum* or *Citrus unshiu* peel with the extract of unprocessed *Chrysanthemum indicum* or *Citrus unshiu* peel is used, the mixture is preferably contained in an amount of 0.0001-30 wt % based on the total weight of the composition, and each of the components of the mixture may be used in an amount suitably selected from the range of 0.0001 to 30 wt % based on the total weight of the composition. Preferably, the extracts of the mixture are used in equal amounts.

The cosmetic composition of the present invention can be formulated as a skin lotion, an astringent lotion, a milk lotion, a nourishing cream, a massage cream, an essence, a pack, a foundation, a lipstick or a powder foundation, but the scope of the present invention is not limited thereto.

In addition, components other than the extract in the cosmetic composition can be suitably selected by a skilled in the art depending on the formulation or intended use of the cosmetic composition.

Mode for the Invention

Hereinafter, the present invention will be described in further detail with reference to examples and test examples. It is to be understood, however, that these examples and test examples are for illustrative purposes only and are not to be construed to limit the scope of the present invention.

COMPARATIVE EXAMPLE 1

Preparation of Extract of Unprocessed *Citrus unshiu* Peel 1 kg of dried *Citrus unshiu* peel was added to 5 l of 80% ethanol aqueous solution, extracted three times under reflux, and then dipped at 15° C. for 1 day. The extract was filtered through filter cloth and centrifuged to separate it into the residue and the filtrate. The separated filtrate was concentrated under reduced pressure, thus obtaining 230 g of an extract of unprocessed *Citrus unshiu* peel.

COMPARATIVE EXAMPLE 2

Preparation of Extract of Unprocessed *Chrysanthemum indicum*

1 kg of dried *Chrysanthemum indicum* was added to 5 l of 80% ethanol aqueous solution, extracted three times under reflux, and then dipped at 15° C. for 1 day. The extract was filtered through filter cloth and centrifuged to separate it into the residue and the filtrate. The separated filtrate was concentrated under reduced pressure, thus obtaining 300 g of an extract of unprocessed *Chrysanthemum indicum*.

COMPARATIVE EXAMPLE 3

Preparation of Mixture of Extracts of Unprocessed *Citrus unshiu* Peel and *Chrysanthemum indicum*

50 g of the unprocessed *Citrus unshiu* peel extract of Comparative Example 1 and 50 g of the unprocessed *Chrysanthemum indicum* extract of Comparative Example 2 were mixed with each other, dissolved completely in 500 ml of 80% ethanol aqueous solution, and then dipped at 15° C. for 1 day. Then, the mixture solution was filtered through filer cloth and centrifuged to separate it into the residue and the filtrate. The separated filtrate was concentrated under reduced pressure, thus obtaining 80 g of a mixture of extracts of unprocessed *Citrus unshiu* peel and *Chrysanthemum indicum*.

EXAMPLE 1

Preparation of Extract of Honey-roasted *Citrus unshiu* Peel 300 g of honey was sufficiently absorbed into 1 kg of dried *Citrus unshiu* peel. The honeyed plant was roasted at 150° C. for 15 minutes, and then dried in the shade. The honey-roasted plant was added to 5 l of 80% ethanol aqueous solution, extracted three times under reflux, and then dipped at 15° C. for 1 day. The extract was filtered through filter cloth and centrifuged to separate it into the residue and the filtrate. The separated filtrate was concentrated under reduced pressure, thus obtaining 315 g of an extract of honey-roasted *Citrus unshiu* peel.

EXAMPLE 2

Preparation of Extract of Honey-roasted *Chrysanthemum indicum*

300 g of honey was sufficiently absorbed into 1 kg of dried *Chrysanthemum indicum*. The honeyed plant was roasted at 150° C. for 15 minutes, and then dried in the shade. The honey-roasted plant was added to 5 l of 80% ethanol aqueous solution, extracted three times under reflux, and then dipped at 15° C. for 1 day. The extract was filtered through filter cloth and centrifuged to separate it into the residue and the filtrate. The separated filtrate was concentrated under reduced pressure, thus obtaining 460 g of an extract of honey-roasted *Chrysanthemum indicum*.

EXAMPLE 3

Preparation of Mixture of Extracts of Unprocessed *Citrus unshiu* Peel and Honey-roasted *Chrysanthemum indicum*

50 g of the unprocessed *Citrus unshiu* peel extract of Comparative Example 1 and 50 g of the honey-roasted *Chrysanthemum indicum* extract of Example 2 were mixed with each other, dissolved completely in 500 ml of 80% ethanol aqueous solution, and then dipped at 15° C. for 1 day. Then, the mixture solution was filtered through filer cloth and centrifuged to separate it into the residue and the filtrate. The separated filtrate was concentrated under reduced pressure, thus obtaining 94 g of a mixture of extracts of unprocessed *Citrus unshiu* peel and honey-roasted *Chrysanthemum indicum*.

EXAMPLE 4

Preparation of Mixture of Extracts of Honey-roasted *Citrus unshiu* Peel and Unprocessed *Chrysanthemum indicum*

50 g of the honey-roasted *Citrus unshiu* peel extract of Example 1 and 50 g of the unprocessed *Chrysanthemum indicum* extract of Comparative Example 2 were mixed with each other, dissolved completely in 500 ml of 80% ethanol aqueous solution, and then dipped at 15° C. for 1 day. Then, the mixture solution was filtered through filer cloth and centrifuged to separate it into the residue and the filtrate. The separated filtrate was concentrated under reduced pressure, thus obtaining 90 g of a mixture of extracts of honey-roasted *Citrus unshiu* peel and unprocessed *Chrysanthemum indicum*

EXAMPLE 5

Preparation of Mixture of Extracts of Honey-roasted *Citrus unshiu* Peel and *Chrysanthemum indicum*

50 g of the honey-roasted *Citrus unshiu* peel extract of Example 1 and 50 g of the honey-roasted *Chrysanthemum indicum* extract of Example 2 were mixed with each other, dissolved completely in 500 ml of 80% ethanol aqueous solution, and then dipped at 15° C. for 1 day. Then, the mixture solution was filtered through filer cloth and centrifuged to separate it into the residue and the filtrate. The separated filtrate was concentrated under reduced pressure, thus obtaining 95 g of a mixture of extracts of honey-roasted *Citrus unshiu* peel and *Chrysanthemum indicum*.

TEST EXAMPLE 1

Test of Antioxidant Effect (DPPH test)

To examine the antioxidant effects of the extracts and mixtures thereof prepared in Comparative Examples 1 and 3 and Examples 1 to 5, the antioxidant activities of these extracts and mixtures were evaluated by comparatively measuring the DPPH (1,1-diphenyl-2-picrylhydrazyl) DPPH oxidation inhibitory effects thereof based on the changes in absorbance caused by the reduction of the free radical DPPH (the antioxidant is oxidized). For the extracts obtained in Comparative Examples 1 to 3 and the extracts and mixtures thereof obtained in Examples 1 to 5, the decrease in absorbance caused by the inhibition of oxidation of DPPH compared to the control was measured, and the concentration at which the absorbance was 50% of the control was defined as the effective antioxidant concentration.

10 μl of each of the materials obtained in Comparative Examples 1 to 3 or Examples 1 to 5 and a positive control sample was added to 190 μl of a solution of 100 μM DPPH in ethanol to prepare a reaction solution. The reaction solution was allowed to react at 37° C. for 30 minutes, and then measured for absorbance at 540 nm. As the positive control, the widely used synthetic antioxidant Trolox was used. The results of DPPH analysis of each of the materials are shown in Table 1 below. In Table 1, $IC_{50}$ means the sample concentration at which the absorbance is reduced by 50%.

TABLE 1

| Sample | | $IC_{50}$ (ppm) |
|---|---|---|
| \multicolumn{3}{l}{DPPH analysis results (inhibition %)} |
| Trolox | | 45 |
| Comp. Ex. 1 | Extract of unprocessed *Citrus unshiu* peel | 98 |
| Comp. Ex. 2 | Extract of unprocessed *Chrysanthemum indicum* | 87 |
| Comp. Ex. 3 | Mixture of extracts of unprocessed *Citrus unshiu* peel and *Chrysanthemum indicum* | 88 |
| Example 1 | Extract of honey-roasted *Citrus unshiu* peel | 35 |
| Example 2 | Extract of honey-roasted *Chrysanthemum indicum* | 37 |
| Example 3 | Mixture of extracts of unprocessed *Citrus unshiu* peel and honey-roasted *Chrysanthemum indicum* | 60 |
| Example 4 | Mixture of extracts of honey-roasted *Citrus unshiu* peel and unprocessed *Chrysanthemum indicum* | 23 |
| Example 5 | Mixture of extracts of honey-roasted *Citrus unshiu* peel and *Chrysanthemum indicum* | 54 |

As can be seen in Table 1 above, the antioxidant activities of the extracts of honey-roasted plants, prepared in Examples 1 to 5, were significantly superior to those of the extracts of unprocessed plants, prepared in Comparative Examples 1 to 3. In addition, the antioxidant effects of the extracts prepared in Examples 1 to 5 were also significantly superior to that of the synthetic antioxidant Trolox used as the positive control.

In the case of the mixtures of the extract of the processed plant and the extract of the unprocessed plant, the mixture of Example 4 containing the honey-roasted *Citrus unshiu* peel extract and the unprocessed *Chrysanthemum indicum* extract showed the highest antioxidant activity which was also significantly superior to that of Trolox.

FORMULATION EXAMPLE 1

Milk Lotion

A milk lotion containing a mixture of extracts of unprocessed *Chrysanthemum indicum* and honey-roasted *Citrus unshiu* peel was prepared to have the composition shown in Table 2 below (unit: wt %).

TABLE 2

| Ingredients | Content |
|---|---|
| Example 4 | 5.0 |
| Squalane | 5.0 |
| Bees Wax | 4.0 |
| Polysorbate 60 | 1.5 |
| Sorbitan sesquioleate | 1.5 |
| Liquid paraffin | 0.5 |
| Caprylic/Capric Triglyceride | 5.0 |
| Glycerin | 3.0 |
| Butylene Glycol | 3.0 |
| Propylene Glycol | 3.0 |
| Carboxyvinyl polymer | 0.1 |
| Triethanol amine | 0.2 |
| Preservative, Pigment, Perfume | Proper Amount |
| Purified water | Balance |
| Total | 100 |

FORMULATION EXAMPLE 2

Skin Lotion

A skin lotion containing a mixture of extracts of unprocessed *Chrysanthemum indicum* and honey-roasted *Citrus unshiu* peel was prepared to have the composition shown in Table 3 below (unit: wt %).

TABLE 3

| Ingredients | Content |
|---|---|
| Example 4 | 5.0 |
| Glycerin | 3.0 |
| Butylene Glycol | 2.0 |
| Propylene Glycol | 2.0 |
| Carboxyvinyl polymer | 0.1 |
| PEG 12 Nonylphenyl Ether | 0.2 |
| Polysorbate 80 | 0.4 |
| Ethanol | 10.0 |
| Triethanol amine | 0.1 |
| Preservative, Pigment, Perfume | Proper Amount |
| Purified water | Balance |
| Total | 100 |

FORMULATION EXAMPLE 3

Nourishing Cream

A nourishing cream containing a mixture of extracts of unprocessed *Chrysanthemum indicum* and honey-roasted *Citrus unshiu* peel was prepared to have the composition chown in Table 4 below (unit. wt %).

TABLE 4

| Ingredients | Content |
|---|---|
| Example 4 | 5.0 |
| Polysorbate 60 | 1.5 |

TABLE 4-continued

| Ingredients | Content |
| --- | --- |
| Sorbitan sesquioleate | 0.5 |
| PEG60 hydrogenated castor oil | 2.0 |
| Liquid paraffin | 10.0 |
| Squalane | 5.0 |
| Caprylic/Capric Triglyceride | 5.0 |
| Glycerin | 5.0 |
| Butylene Glycol | 3.0 |
| Propylene Glycol | 3.0 |
| Triethanol amine | 0.2 |
| Preservative, Pigment, Perfume | Proper Amount |
| Purified water | Balance |
| Total | 100 |

FORMULATION EXAMPLE 4

Massage Cream

A massage cream containing a mixture of extracts of unprocessed *Chrysanthemum indicum* and honey-roasted *Citrus unshiu* peel was prepared to have the composition shown in Table 5 below (unit: wt %).

TABLE 5

| Ingredients | Content |
| --- | --- |
| Example 4 | 5.0 |
| Bees Wax | 10.0 |
| Polysorbate 60 | 1.5 |
| Sorbitan sesquioleate | 0.8 |
| PEG60 hydrogenated castor oil | 2.0 |
| Liquid paraffin | 40.0 |
| Squalane | 5.0 |
| Caprylic/Capric Triglyceride | 4.0 |
| Glycerin | 5.0 |
| Butylene Glycol | 3.0 |
| Propylene Glycol | 3.0 |
| Triethanol amine | 0.2 |
| Preservative, Pigment, Perfume | Proper Amount |
| Purified water | Balance |
| Total | 100 |

FORMULATION EXAMPLE 5

Pack

A pack containing a mixture of extracts of unprocessed *Chrysanthemum indicum* and honey-roasted *Citrus unshiu* peel was prepared to have the composition shown in Table 6 below (unit: wt %).

TABLE 6

| Ingredients | Content |
| --- | --- |
| Example 4 | 5.0 |
| Polyvinyl Acohol | 13.0 |
| Sodium Carboxymethyl Cellulose | 0.2 |
| Glycerin | 5.0 |
| Allantoin | 0.1 |
| Ethanol | 6.0 |
| PEG 12 Nonylphenyl Ether | 0.3 |
| Polysorbate 60 | 0.3 |
| Preservative, Pigment, Perfume | Proper Amount |
| Purified water | Balance |
| Total | 100 |

The invention claimed is:

1. An antioxidant cosmetic composition which contains, as an active ingredient, a mixture of a honey-added and roasted *Chrysanthemum indicum* extract and a honey-added and roasted *Citrus unshiu* peel extract,
    wherein the mixing ratio of the honey-added and roasted *Citrus unshiu* peel extract and the *Chrysanthemum indicum* extract is 1:1, and
    wherein each of the honey-added and roasted *Chrysanthemum indicum* extract and honey-added and roasted *Citrus unshiu* peel extract is prepared through a method comprising the steps of:
        a) adding honey to *Chrysanthemum indicum* or *Citrus unshiu* peel and allowing the added honey to be absorbed into the plant for 30 minutes to 1 hour;
        b) roasting the plant of step a) at 100-180° C. for 10 minutes to 1 hour; and
        c) extracting the roasted *Chrysanthemum indicum* or *Citrus unshiu* peel of step b) with water or an organic solvent.

2. The antioxidant cosmetic composition of claim 1, wherein the composition further contains at least one of *Chrysanthemum indicum* extract and *Citrus unshiu* peel extract, and each of the *Chrysanthemum indicum* extract and *Citrus unshiu* peel extract is prepared from a plant different from a plant used to prepare the honey-added and roasted *Chrysanthemum indicum* extract and honey-added and roasted *Citrus unshiu* peel extract,
    wherein the *Chrysanthemum indicum* extract and the *Citrus unshiu* peel extract are an extract obtained by extracting each of *Chrysanthemum indicum* and *Citrus unshiu* peel with water or an organic solvent.

3. The antioxidant cosmetic composition of claim 1, wherein the organic solvent is at least one selected from the group consisting of ethanol, methanol, butanol, ether, ethyl acetate, chloroform, and mixtures of these solvents with water.

4. The antioxidant cosmetic composition of claim 1, wherein the honey-added and roasted *Chrysanthemum indicum* extract and the honey-added and roasted *Citrus unshiu* peel extract are respectively or mixedly contained in an amount of 0.0001-30 wt % based on the total weight of the composition.

5. The antioxidant cosmetic composition of claim 2, wherein said composition is a mixture of the extract of at least one of the honey-added and roasted *Chrysanthemum indicum* extract and the honey-added and roasted *Citrus unshiu* peel extract, and the extract of at least one of the *Chrysanthemum indicum* extract and the *Citrus unshiu* peel extract is contained in an amount of 0.0001-30 wt % based on the total weight of the composition.

6. The antioxidant cosmetic composition of claim 2, wherein the organic solvent is ethanol.

7. The antioxidant cosmetic composition of claim 3, wherein the organic solvent is ethanol.

8. The antioxidant cosmetic composition of claim 7, wherein the ethanol is 80% ethanol.

9. The antioxidant cosmetic composition of claim 1, wherein said honey-added and roasted *Chrysanthemum indicum* extract has a DPPH oxidation inhibitory effect that is at least two folds more than *Chrysanthemum indicum* extract which is not honey-added and roasted; and wherein said honey-added and roasted *Citrus unshiu* peel extract has a DPPH oxidation inhibitory effect that is at least two folds more than *Citrus unshiu* peel extract which is not honey-added and roasted.

10. The antioxidant cosmetic composition of claim 1, wherein the organic solvent is ethanol.

\* \* \* \* \*